(12) United States Patent
Parker et al.

(10) Patent No.: US 8,170,252 B2
(45) Date of Patent: May 1, 2012

(54) DUAL PERCUTANEOUS ANCHORS BONE CONDUCTION DEVICE

(75) Inventors: John Parker, Roseville (AU); Gunnar Kristian Asnes, Molndal (SE)

(73) Assignee: Cochlear Limited, Macquarie University, NSW (AU)

( * ) Notice: Subject to any disclaimer, the term of this patent is extended or adjusted under 35 U.S.C. 154(b) by 904 days.

(21) Appl. No.: 12/168,653

(22) Filed: Jul. 7, 2008

(65) Prior Publication Data
US 2009/0247812 A1 Oct. 1, 2009

Related U.S. Application Data

(60) Provisional application No. 61/041,185, filed on Mar. 31, 2008.

(51) Int. Cl.
*H04R 25/00* (2006.01)
(52) U.S. Cl. ............... 381/326; 381/151; 600/25
(58) Field of Classification Search ......... 381/326, 381/151; 600/25
See application file for complete search history.

(56) References Cited

U.S. PATENT DOCUMENTS

| 4,025,964 | A | * | 5/1977 | Owens ............... 623/11.11 |
| 4,904,233 | A | * | 2/1990 | Håkansson et al. ....... 600/25 |
| 6,643,378 | B2 | | 11/2003 | Schumaier |
| 6,840,919 | B1 | * | 1/2005 | Håkansson ............ 604/175 |
| 7,065,223 | B2 | * | 6/2006 | Westerkull ............ 381/326 |
| 2006/0056649 | A1 | | 3/2006 | Schumaier |
| 2006/0126874 | A1 | * | 6/2006 | Westerkull ............ 381/326 |
| 2010/0137675 | A1 | * | 6/2010 | Parker ................. 600/25 |

FOREIGN PATENT DOCUMENTS

| WO | 0193645 | 12/2001 |
| WO | 2004093401 | 10/2004 |
| WO | 2005000391 | 1/2005 |

* cited by examiner

*Primary Examiner* — Steven Loke
*Assistant Examiner* — David Goodwin
(74) *Attorney, Agent, or Firm* — Kilpatrick, Townsend & Stockton, LLP.

(57) ABSTRACT

A bone conduction device for enhancing the hearing of a recipient, comprising: a sound input element configured to receive an acoustic sound signal; an electronics module configured generate an electrical signal representing the acoustic sound signal; a transducer configured to generate mechanical forces representing the electrical signal for deliver to the recipient's skull; and dual percutaneous anchors coupled to the transducer and configured to receive and transmit the mechanical forces.

26 Claims, 6 Drawing Sheets

DUAL PERCUTANEOUS ANCHORS BONE CONDUCTION DEVICE

CROSS-REFERENCE TO RELATED APPLICATIONS

The present application claims the benefit of U.S. Provisional Patent Application 61/041,185; filed Mar. 31, 2008, which is hereby incorporated by reference herein.

BACKGROUND

1. Field of the Invention

The present invention is generally directed to a bone conduction device, and more particularly, to a dual percutaneous anchors bone conduction device 2. Related Art Hearing loss, which may be due to many different causes, is generally of two types, conductive or sensorineural. In many people who are profoundly deaf, the reason for their deafness is sensorineural hearing loss. This type of hearing loss is due to absence, destruction, or damage to the hairs that transduce acoustic signals into nerve impulses in the cochlea. Various prosthetic hearing implants have been developed to provide individuals who suffer from sensorineural hearing loss with the ability to perceive sound. One type of prosthetic implant, referred to as a cochlear implant, uses an electrode array implanted in the cochlea. More specifically, an electrical stimulus is provided via the electrode array directly to the cochlea nerve, thereby inducing a hearing sensation in the implant recipient.

Conductive hearing loss occurs when the normal mechanical pathways, which conduct sound to hairs in the cochlea, are impeded. This problem may arise from damage to the ossicular chain to ear canal. However, individuals who suffer from conductive hearing loss frequently still have some form of residual hearing because the hairs in the cochlea are often undamaged. For this reason, individuals who suffer from conductive hearing loss are typically not candidates for a cochlear implant, because insertion of the electrode array into a cochlea results in the severe damage or destruction of the most of the hairs within the cochlea.

Sufferers of conductive hearing loss typically receive an acoustic hearing aid. Hearing aids receive ambient sound in the outer ear, amplify the sound, and direct the amplified sound into the ear canal. The amplified sound reaches the cochlea and causes motion of the cochlea fluid, thereby stimulating the hairs in the cochlea.

Unfortunately, hearing aids do not benefit all individuals who suffer from conductive hearing loss. For example, some individuals are prone to chronic inflammation or infection of the ear canal and cannot wear hearing aids. Other individuals have malformed or absent outer ear and/or ear canals as a result of a birth defect, or as a result of common medical conditions such as Treacher Collins syndrome or Microtia. Hearing aids are also typically unsuitable for individuals who suffer from single-sided deafness (i.e., total hearing loss only in one ear) or individuals who suffer from mixed hearing losses (i.e., combinations of sensorineural and conductive hearing loss).

Those individuals who cannot benefit from hearing aids may benefit from hearing prostheses that are implanted into the skull bone. Such hearing prostheses direct vibrations into the bone, so that the vibrations are conducted into the cochlea and result in stimulation of the hairs in the cochlea. This type of prosthesis is typically referred to as a bone conduction device.

Bone conduction devices function by converting a received sound into a mechanical vibration representative of the received sound. This vibration is then transferred to the bone structure of the skull, causing vibration of the recipient's skull and serves to stimulate the cochlea hairs, thereby inducing a hearing sensation in the recipient.

SUMMARY

According to one aspect of the present invention, there is provided a bone conduction device for enhancing the hearing of a recipient, comprising: a sound input element configured to receive an acoustic sound signal; an electronics module configured generate an electrical signal representing the acoustic sound signal; a transducer configured to generate mechanical forces representing the electrical signal for deliver to the recipient's skull; and dual percutaneous anchors coupled to the transducer and configured to receive and transmit the mechanical forces.

According to another aspect of the present invention, there is provided a method for rehabilitating the hearing of a recipient with a bone conduction device having dual percutaneous anchors, comprising: forming a mechanical coupling between the bone conduction device and the recipient's skull via the dual percutaneous anchors; receiving an electrical signal representative of an acoustic sound signal; generating mechanical forces representative of the received electrical signal; and delivering the mechanical forces to the recipient's skull via the formed coupling.

According to yet another aspect of the present invention, there is provided a bone conduction device for enhancing the hearing of a recipient, having dual percutaneous anchors, comprising: means for forming a mechanical coupling between the bone conduction device and the recipient's skull via the dual percutaneous anchors; means for receiving an electrical signal representative of an acoustic sound signal; means for generating mechanical forces representative of the received electrical signal; and means for delivering the mechanical forces to the recipient's skull via the formed coupling.

BRIEF DESCRIPTION OF THE DRAWINGS

Illustrative embodiments of the present invention are described herein with reference to the accompanying drawings, in which.

DETAILED DESCRIPTION

Embodiments of the present invention are generally directed to a bone conduction device for converting a received acoustic sound signal into a mechanical force delivered via a recipient's skull to the recipient's hearing organs. The bone conduction device includes a sound input component, such as microphone, to receive the acoustic sound signal, an electronics module configured to generate an electrical signal representing the acoustic sound signal, a transducer to convert the electrical signal into a mechanical force for delivery to the recipient's skull, and dual implanted percutaneous anchors to transmit the mechanical force received from the transducer to the recipient's skull. In certain embodiments of the present invention, the dual percutaneous anchors are coupled to the bone conduction device at a bottom surface of the device adjacent the recipient's skull, while in other embodiments of the present invention, the dual percutaneous anchors are coupled to the bone conduction device at opposite sides of the device. The transducer of the bone conduction device generates and transfers mechanical forces to the dual percutaneous anchors simultaneously and in opposite directions such that the dual percutaneous anchors move in opposite directions with respect to one another. By vibrating the dual percutaneous anchors in opposite directions, the bone conduction device of the present invention transmits mechanical forces to the recipient's skull while avoiding rotating or otherwise applying torque force on the recipient's skull or head.

The output stroke of the transducer (sometimes referred to herein as the "transducer stroke") is utilized to generate a mechanical force that may be provided to the recipient's skull. The sound perceived by a recipient is dependent, in part, upon the magnitude of mechanical force generated by the transducer. In some bone conduction devices, the magnitude of the mechanical force may be limited by the available transducer stroke. These limitations may cause distortion in the sound signal perceived by the recipient or limit the population of recipient's that may benefit from the device. For example, in certain embodiments, limited transducer stroke results in insufficient gain to adequately represent a received acoustic sound signal for all individuals. This insufficient gain may cause a signal to be clipped or otherwise distorted.

In certain embodiments of the present invention, the transducer may comprise a piezoelectric element. The piezoelectric element converts an electrical signal applied thereto into a mechanical deformation (i.e. expansion or contraction) of the element. The amount of deformation of a piezoelectric element in response to an applied electrical signal depends on material properties of the element, orientation of the electric field with respect to the polarization direction of the element, geometry of the element, etc.

The deformation of the piezoelectric element may also be characterized by the free stroke and blocked force of the element. The free stroke of a piezoelectric element refers to the magnitude of deformation induced in the element when a given voltage is applied thereto. Blocked force refers to the force that must be applied to the piezoelectric element to stop all deformation at the given voltage. Generally speaking, piezoelectric elements have a high blocked force, but a low free stroke. In other words, when a voltage is applied to the element, the element will can output a high force, but will only produce a small stroke.

As noted, bone conduction devices generate a mechanical force that is delivered to the skull, thereby causing motion of the cochlea fluid and a hearing perception by the recipient. In some piezoelectric transducers, the maximum available transducer stroke is equivalent to the free stroke of the piezoelectric element. As such, some bone conduction devices utilizing these types of piezoelectric transducer have a limited transducer stroke and corresponding limits on the magnitude of the mechanical force that may be provided to the skull.

Figure 1:
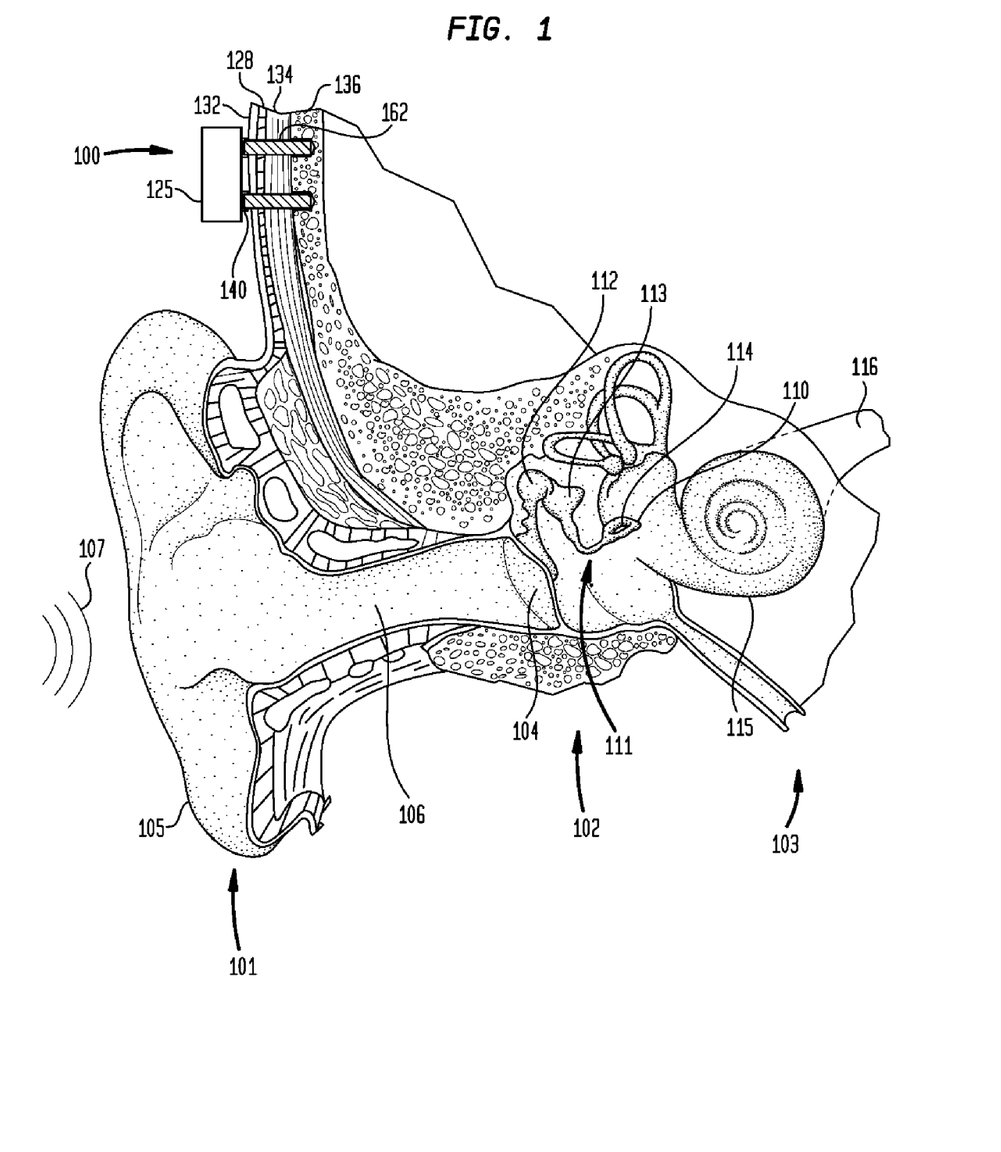
FIG. 1 is a perspective view of a dual percutaneous anchors bone conduction device provided to a recipient according to one embodiment of the present invention.

FIG. 1 is a perspective view of embodiments of a bone conduction device 100 in which embodiments of the present invention may be advantageously implemented. In a fully functional human hearing anatomy, outer ear 105 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient.

In the embodiments illustrated in FIG. 1, bone conduction device 100 comprises a housing 125 having a microphone (not shown) positioned therein or thereon. Housing 125 is coupled to the body of the recipient via an anchoring system comprising coupling 140 and implanted dual percutaneous anchors 162. As described below, bone conduction device 100 may comprise a sound processor, a transducer, transducer drive components, an anchoring system, and/or various other circuits/components.

Figure 2A:
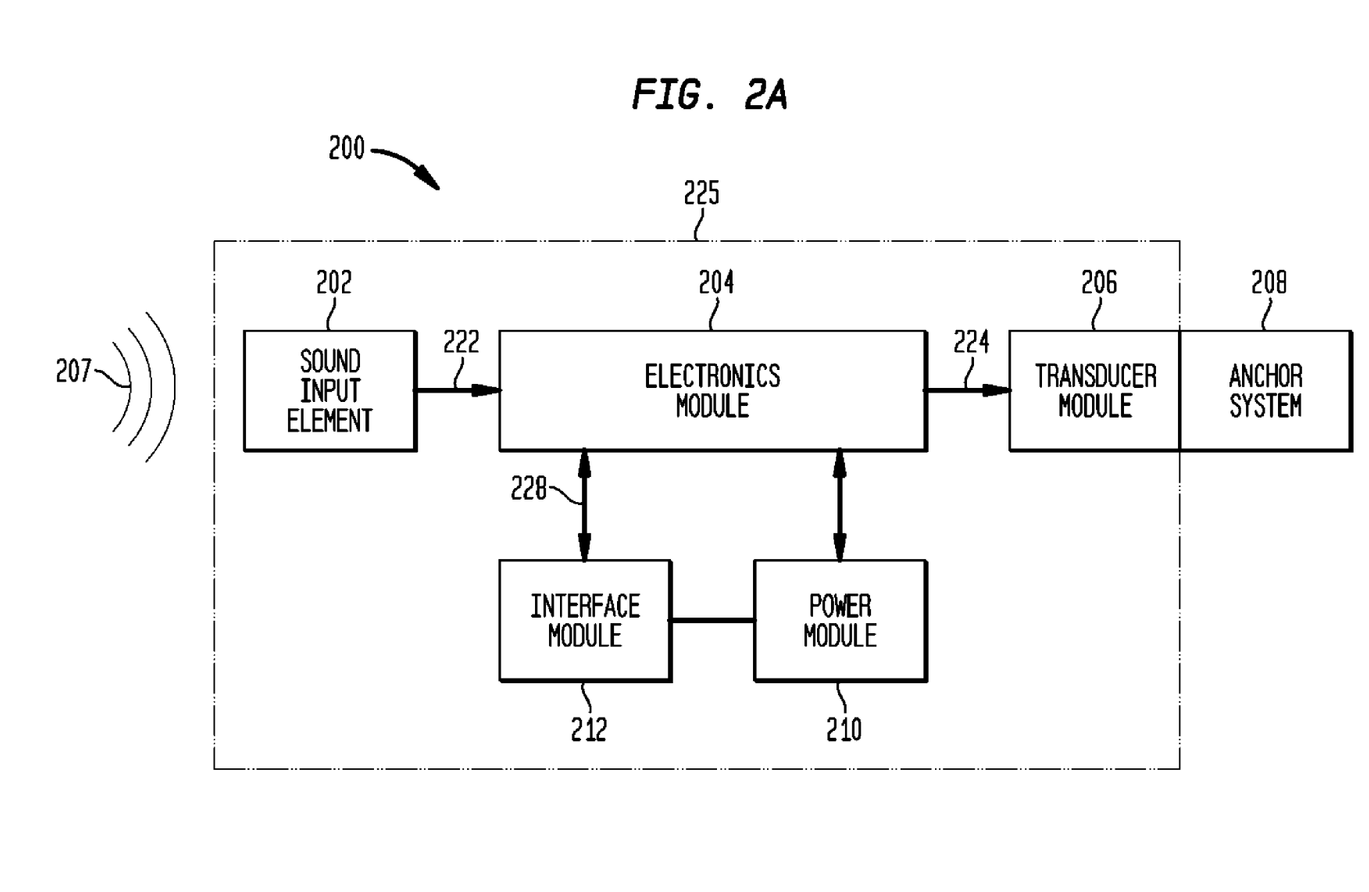
FIG. 2A is a high-level functional block diagram of a dual percutaneous anchors bone conduction device according to one embodiment of the present invention, such as the device of FIG. 1.
Figure 2B:
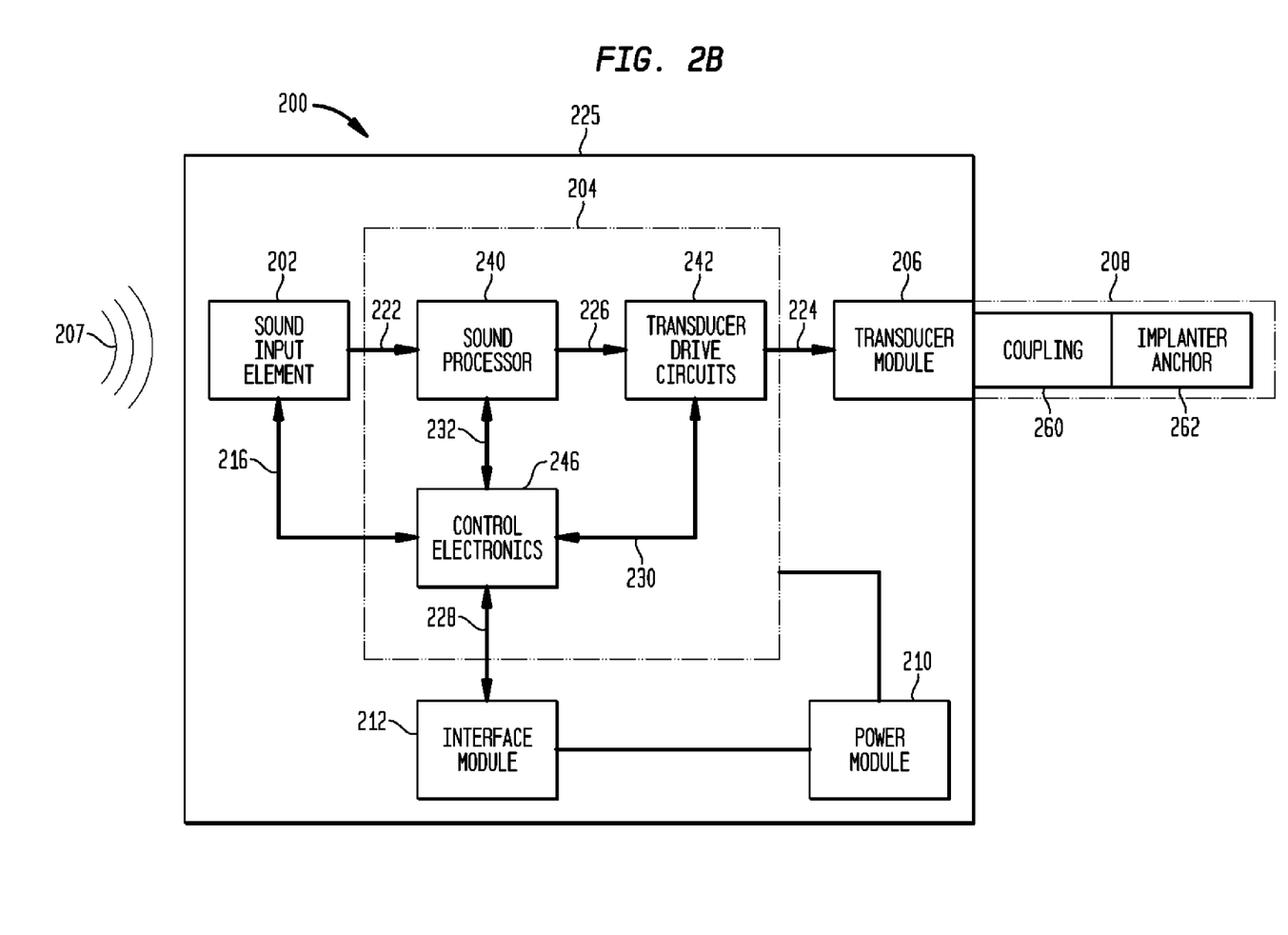
FIG. 2B is a detailed functional block diagram of the dual percutaneous anchors bone conduction device illustrated in FIG. 2A.

In accordance with embodiments of the present invention, an anchor system as described in conjunction with FIGS. 2A and 2B may be at least partially implanted in the recipient. As described below, the anchor system may be fixed to bone 136. In various embodiments, the anchor system may be surgically placed through skin 132, muscle 134 and/or fat 128. In certain embodiments, the anchor system may comprise a coupling 140 and one or more anchoring elements 162.

A functional block diagram of one embodiment of bone conduction device 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, transducer 206 receives adjusted electrical signal 224 and generates a mechanical output force that is delivered to the skull of the recipient via anchor system 208 which is coupled to bone conduction device 200.

FIG. 2A also illustrates a power module 210. Power module 210 provides electrical power to one or more components of bone conduction device 200. For ease of illustration, power module 210 has been shown connected only to interface module 212 and electronics module 204. However, it should be appreciated that power module 210 may be used to supply power to any electrically powered circuits/components of bone conduction device 200.

Bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2A, sound pickup device 202, electronics module 204, transducer 206, power module 210 and interface module 212 have all been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

In embodiments of the present invention, transducer 206 may be one of many types and configurations of transducers, now known or later developed. In one embodiment of the present invention, transducer 206 may comprise a piezoelectric element which is configured to deform in response to the application of electrical signal 224. Piezoelectric elements that may be used in embodiments of the present invention may comprise, for example, piezoelectric crystals, piezoelectric ceramics, or some other material exhibiting a deformation in response to an applied electrical signal. Exemplary piezoelectric crystals include quartz ($SiO_2$), Berlinite ($AlPO_4$), Gallium orthophosphate ($GaPO_4$) and Tourmaline. Exemplary piezoelectric ceramics include barium titanate ($BaTiO_3$0), lead zirconate titanate (PZT), or zirconium (Zr).

Some piezoelectric materials, such as barium titanate and PZT, are polarized materials. When an electric field is applied across these materials, the polarized molecules align themselves with the electric field, resulting in induced dipoles within the molecular or crystal structure of the material. This alignment of molecules causes the deformation of the material.

In other embodiments of the present invention, other types of transducers may be used. For example, various motors configured to operate in response to electrical signal 224 may be used.

Transducer 206 is configured to generate substantially lateral mechanical forces that are parallel to the surface of recipient's skull 136. Transducer 206 is coupled to two anchors (not shown), also referred to as "dual percutaneous anchors", on opposite ends of transducer 206, and as a result the dual percutaneous anchors receive substantially equal forces exerted by transducer 206 in opposite directions. Delivery of this output force causes one or more of motion or vibration of the recipient's skull, thereby activating the hair cells in the cochlea via cochlea fluid motion. While the recipient's skull, particularly in the portions thereof in the area where the dual percutaneous anchors are implanted, are caused to bend, flex, move, vibrate, or otherwise change its position because of the forces transferred via the dual percutaneous anchors moving in opposite directions from one other, the bone conduction device 200 produces no net rotation or translation force on the recipient's head.

In certain embodiments of the present invention, electronics module 204 includes a printed circuit board (PCB) to electrically connect and mechanically support the components of electronics module 204. Sound input element 202 may comprise one or more microphones (not shown) and is attached to the PCB.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 224A is provided to transducer drive components 242. Transducer drive components 242 output a drive signal 224B, to transducer 206. Based on drive signal 224B, transducer 206 provides the output force to the skull of the recipient.

For ease of description the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, in one embodiment of the present invention, anchor system 208 comprises external couplings 260 which couples to dual percutaneous anchors 262. Coupling 260 may be attached to one or more of transducer 206 or housing 225. For example, in certain embodiments, coupling 260 is attached to transducer 206 and vibration is received directly therefrom. In other embodiments, coupling 260 is attached to housing 225 and vibration is applied from transducer 206 through housing 225 to coupling 260. According to one embodiment of the present invention in which coupling 140 comprises coupling 260 which couples mechanically to transducer 206, the vibration received by coupling 260 from transducer 206 causes coupling 260 to vibrate. Since, according to this embodiment of the present invention, couplings 260 is mechanically coupled to dual percutaneous anchors 262, dual percutaneous anchors 262 also vibrates. The vibration, communicated from coupling 260 to dual percutaneous anchors 262 mechanically is then transferred from dual percutaneous anchors 262 to the recipient's bone 136.

In addition to mechanical couplings between dual percutaneous anchors 262 described above, certain embodiments of the present invention may also utilize other types of couplings between dual percutaneous anchors 262 and transducer 206 or housing 225. For example, dual percutaneous anchors 262 may be magnetically coupled to housing 225 or to transducer 206 such that the mechanical forces generated by transducer 206 are transmitted magnetically to dual percutaneous anchors 262. Furthermore, although transducer 206 and dual percutaneous anchors 262 have been presently described as two separate components, it is to be understood that transducer 206 and dual percutaneous anchors 262 as described herein may be manufactured as a single or unitary component or manufactured separately and permanently joined together.

Bone conduction device 200 may further comprise an interface module 212. Interface module 212 includes one or more components that allow the recipient to provide inputs to, or receive information from, elements of bone conduction device 200.

As shown, control electronics 246 may be connected to one or more of interface module 212, sound pickup device 202, sound processor 240 and/or transducer drive components 242. In embodiments of the present invention, based on inputs received at interface module 212, control electronics 246 may provide instructions to, or request information from, other components of bone conduction device 200. In certain embodiments, in the absence of user inputs, control electronics 246 control the operation of bone conduction device 200.

Figure 3:
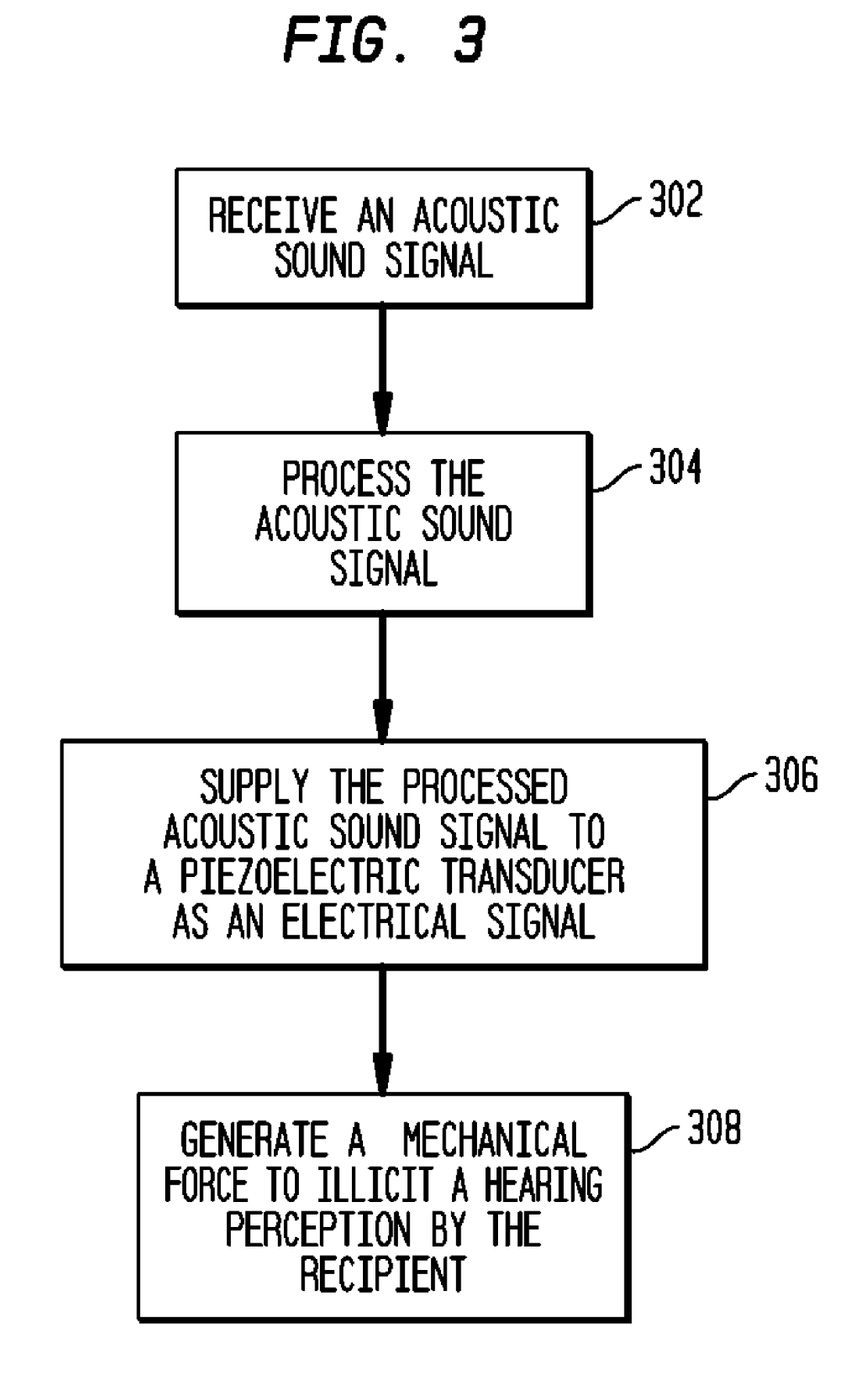
FIG. 3 is a flowchart illustrating the conversion of an input sound into skull vibration in a dual percutaneous anchors bone conduction device according to one embodiment of the present invention.

FIG. 3 illustrates the conversion of an input acoustic sound signal into a mechanical force for delivery to the recipient's skull in accordance with embodiments of bone conduction device 200. At block 302, bone conduction device 200 receives an acoustic sound signal. In certain embodiments, the acoustic sound signal is received via microphones. In other embodiments, the input sound is received via an electrical input. In still other embodiments, a telecoil integrated in, or connected to, bone conduction device 200 may be used to receive the acoustic sound signal.

At block 304, the acoustic sound signal received by bone conduction device 200 is processed by the speech processor in electronics module 204. As explained above, the speech processor may be similar to speech processors used in acoustic hearing aids. In such embodiments, speech processor may selectively amplify, filter and/or modify acoustic sound signal. For example, speech processor may be used to eliminate background or other unwanted noise signals received by bone conduction device 200.

At block 306, the processed sound signal is provided to transducer 206 as an electrical signal. At block 308, transducer 206 converts the electrical signal into a mechanical force configured to be delivered to the recipient's skull via anchor system 208 so as to illicit a hearing perception of the acoustic sound signal.

Figure 4A:
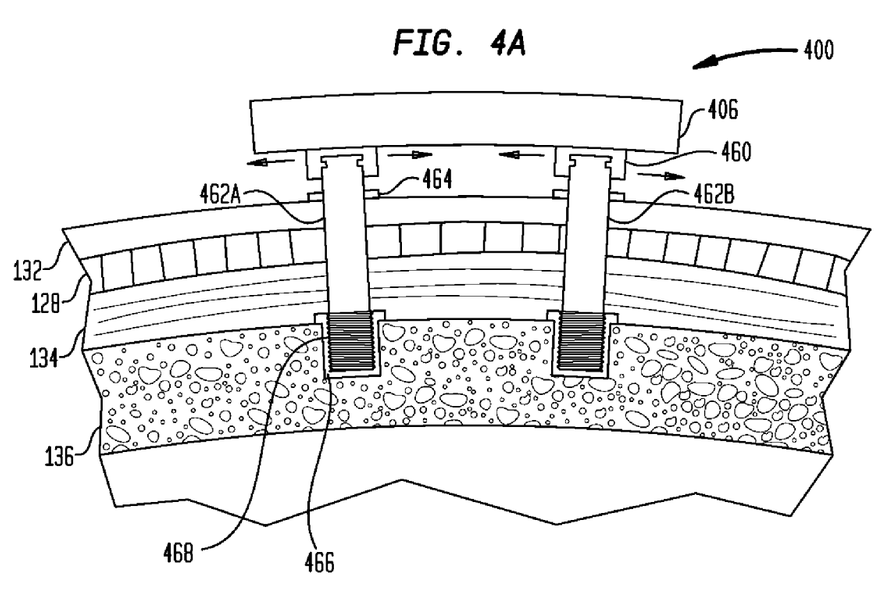
FIG. 4A is a perspective view of a dual percutaneous anchors bone conduction device according to a further embodiment of the present invention.

FIG. 4A illustrates one embodiment of the bone conduction device 400 of the present invention. In the illustrated embodiment, two couplings 460 are shown, one connected to each of dual percutaneous anchors 462A and 462B (collectively referred to as dual percutaneous anchors 462). Couplings 460 deliver the mechanical force (shown as arrows) from the transducer in housing 406 to the recipient's skull 136. As will be appreciated by persons having skill in the art, dual percutaneous anchors 462 may be attached to recipient's skull 136 in a variety of ways. For example, dual percutaneous anchors 462 may have a threaded portion 468 at one end which is to be positioned within or adjacent to recipient's skull 136. A corresponding socket 466 may have corresponding threads to receive the threaded portion 468 such that anchor 462A may be screwed into socket 466 to achieve a secure fixation of anchor 462A and similarly 462B in recipient's skull 136. Alternatively, in one embodiment, anchors 462 may not have a threaded socket as described above but may instead be screwed directly into correspondingly shaped holes (not shown) formed in recipient's skull 136, wherein the threaded end 468 may have releasable compounds which facilitate in the formation of new bone to surround and securely fix the dual percutaneous anchors 462 in recipient's skull 136. Other method of securing anchors 462 in recipient's skull 136, now known or later developed, will be obvious to persons having skill in the art and are considered a part of the present invention.

Figure 4B:
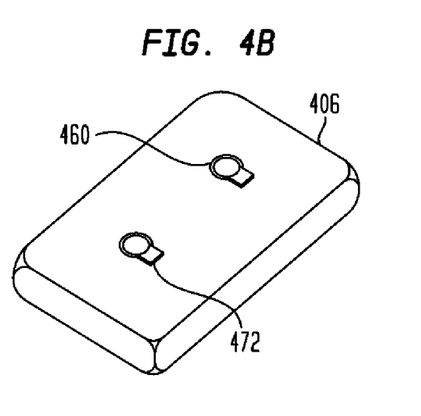
FIG. 4B is a perspective view of a component of the dual percutaneous anchors bone conduction device illustrated in FIG. 4A.
Figure 4C:
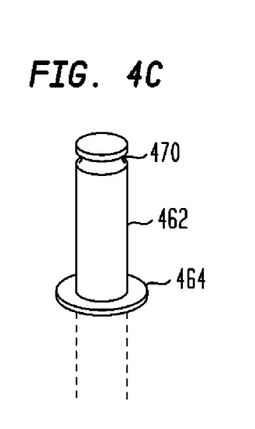
FIG. 4C is a perspective view of components used in conjunction with the dual percutaneous anchors bone conduction device illustrated in FIG. 4A.

FIGS. 4B and 4C illustrate another embodiment of the present invention in which transducer 406 is in its own housing, separate from other components of the present invention (not shown) such as the sound processor (not shown), interface module (not shown) and others. In FIG. 4B, couplings 460 are configured to receive one end of dual percutaneous anchors 470, shown in FIG. 4C. In the embodiment illustrated in FIG. 4B, latch 472 may be operated to release an anchor that has been secured within coupling 460. In other embodiments of the present invention, other securing and release mechanisms may be used, such as fixation screws which may be screwed in and out to secure and release dual percutaneous anchors 462 in couplings 460. Other mechanisms, now known or later developed, will be obvious to person of skill in the art and are considered a part of the present invention.

Also shown in FIGS. 4A and 4C is a ring 464 which is configured to be positioned on the surface of recipient's skin 132 so as to provide a protective shield at the point where anchors 462 emerge through recipient's skin 132. Ring 464 may be made of a flexible material. Ring 464 may also have at least its bottom surface adhered to recipient's skin 132. Furthermore, any gap or space between the hollow center of ring 464 and anchors 462 may be sealed so as to prevent air or moisture from entering or exiting through the opening in recipient's skin 132. By providing ring 464 with a bottom surface adhered to the recipient's skin, and by further sealing any gaps which may otherwise exist between ring 464 and anchors 462, it is possible for the percutaneous dual percutaneous anchors of the present invention to operate over extended periods of time with a greatly reduced risk of liquids and matter entering or leaving the recipient's body, thus reducing various health risks such as infection. Although a relatively simple ring 462 has been described above, it should be understood that more extensive configurations for sealing and securing the recipient's body at the entry points for the dual percutaneous anchors 462 into the recipient's body may be used in conjunction with the present invention.

Figure 5:
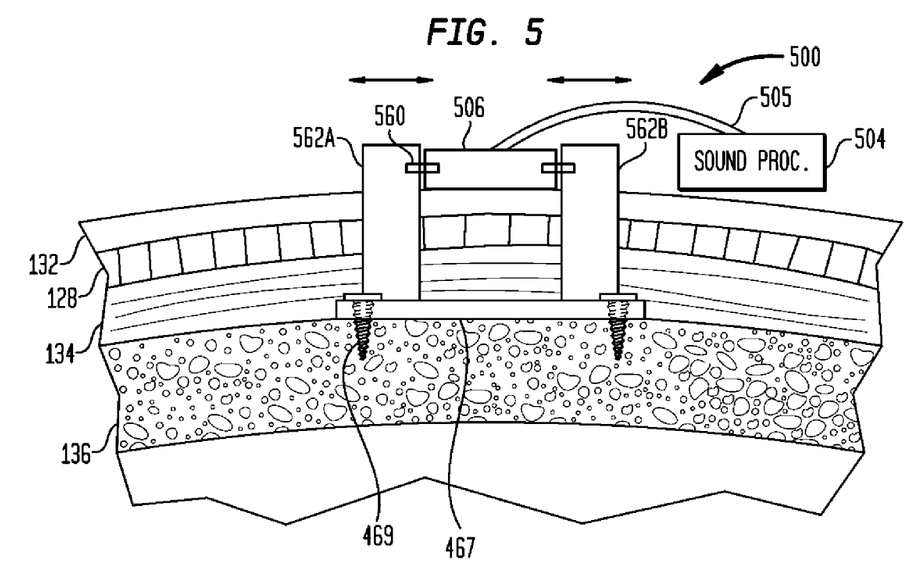
FIG. 5 is a perspective side view of a dual percutaneous anchors bone conduction device according to another embodiment of the present invention.

FIG. 5 illustrate yet another embodiment of the present invention in which dual percutaneous anchors bone conduction device 500 is shown with transducer 506 in a sandwich configuration between dual percutaneous anchors 562A and 562B (collectively referred to herein as anchors 562). Dual percutaneous anchors 562 are mechanically coupled to transducer 506 via connectors 560. Although the embodiment illustrated in FIG. 5 has transducer 506 in a separate housing from sound processor 504 connected by cable 505, as noted above, it is to be understood that in other embodiments of the present invention, transducer 506 and sound processor 504, in addition to other components of the device, may be housed in a single housing.

In another embodiment of the present invention illustrated in FIG. 5, bone conduction device 400 comprises dual percutaneous anchors 562A and 562B (collectively referred to as dual percutaneous anchors 562) coupled to transducer 506 via couplings 560. Couplings 560 may be one of various kinds of coupling mechanisms, now known or later developed, which permit the transmission or delivery of the mechanical forces (shown as arrows) generated by transducer 506 to anchors 562. As described above with respect to FIGS. 2A and 2B, couplings 560 may comprise magnetic or mechanical couplings. In the case of magnetic couplings, as will be obvious to persons having skill in the art, magnets attached to dual percutaneous anchors 560 and correspondingly positioned magnets on transducer 506 may be arranged so that the two sets of magnets are attracted to one another and permit the transmission of the mechanical forces generated by transducer 506 to dual percutaneous anchors 562.

In the embodiment illustrated, transducer 506 is housed separated from sound processor 504 and is connected to sound processor 504 via cable 505. However, it is to be understood that transducer 506 and sound processor 504 may be housed in a single housing 125, as described above. Housing the components separately provides various advantages, as will be obvious to persons having skill in the art, such as flexibility in positioning the various separate components. However, as will also be obvious to persons having skill in the art, housing the various components of the bone conduction device of the present invention in a single housing has its own advantages, including being a simpler device to manufacture, install, operate and maintain.

In one embodiment of the present invention as shown in FIG. 5, dual percutaneous anchors 562 are firmly mounted on plate 567 such that anchors 562 are able to transmit mechanical forces received from transducer 506 to plate 567. Plate 567 is secured in plate using screws 569. In other embodiments of the present invention, plate 567 may be fixed using other securing mechanisms, alone or in combination with screws 569. Plate 567 is sufficiently flexible so as to flex when the opposing mechanical forces (shown as arrows) as described above are transmitted by dual percutaneous anchors 562, such that the opposing mechanical forces are applied to the recipient's skull 136 in the surrounding plate 467.

In one embodiment of the present invention, plate 567 may be flexible as described above. In other embodiments of the present invention plate 567 is inflexibly rigid when subjected to the range of mechanical forces generated by transducer 506. However, plate 567 may be equipped with one or more joints (not shown) or other similar structures which permit the opposing mechanical forces delivered by anchors 562 to be substantially applied to recipient's skull 136.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A bone conduction device for enhancing the hearing of a recipient, comprising:
    a sound input element configured to receive an acoustic sound signal;
    an electronics module configured generate an electrical signal representing said acoustic sound signal;
    a transducer configured to generate mechanical forces substantially parallel to a recipient's skull, wherein the mechanical forces represent said electrical signal; and
    dual percutaneous anchors coupled to said transducer and configured to receive and transmit said mechanical forces.

2. The device of claim 1, wherein said transducer and/or anchors further comprise one or more magnets to couple said transducer to said anchors.

3. The device of claim 1, wherein said transducer comprises one or more piezoelectric elements configured to generate said mechanical forces.

4. The device of claim 1, wherein said transducer and said dual percutaneous anchors are coupled mechanically.

5. The device of claim 1, wherein said transducer is configured to generate said mechanical forces in opposite directions for transmission via said dual percutaneous anchors to the recipient's skull.

6. The device of claim 1, wherein said transducer is mechanically coupled to two or more sockets configured to receive the ends of said dual percutaneous anchors.

7. The device of claim 1, wherein said dual percutaneous anchors are fixedly attached to the recipient's skull.

8. The device of claim 7, wherein said dual percutaneous anchors are configured to be positioned at least partially in recipient's skull, and further configured to osseointegrated with recipient's skull over a period of time.

9. The device of claim 7, wherein said dual percutaneous anchors are fixed by one or more screws to the recipient's skull.

10. The device of claim 7, wherein said dual percutaneous anchors are attached to one or more plates fixed to the recipient's skull.

11. The device of claim 10, wherein said one or more plates further comprises joints.

12. The device of claim 10, wherein said one or more plates are configured to osseointegrate with the recipient's skull over a period of time.

13. A method for rehabilitating the hearing of a recipient with a bone conduction device having dual percutaneous anchors, comprising:
    forming a mechanical coupling between the bone conduction device and the recipient's skull via the dual percutaneous anchors;
    receiving an electrical signal representative of an acoustic sound signal;
    generating mechanical forces representative of the received electrical signal substantially parallel to the recipient's skull; and
    delivering said mechanical forces to the recipient's skull via the formed coupling.

14. The method of claim 13, wherein said formed mechanical coupling comprises a coupling between the dual percutaneous anchors and the device retained by magnet forces.

15. The method of claim 13, wherein said mechanical forces are generated by one or more piezoelectric elements in the device.

16. The method of claim 13, wherein said mechanical forces are generated in two opposing directions for transmission via the dual percutaneous anchors to the recipient's skull, wherein the generated forces produce no net torque forces on the recipient's skull.

17. The method of claim 13, wherein said mechanical forces are generated in parallel to the recipient's bone.

18. The method of claim 13, further comprising:
    securing the dual percutaneous anchors within to the bone conduction device via one or more sockets disposed on the bone conduction device.

19. The method of claim 13, further comprising:
attaching the dual percutaneous anchors to the recipient's skull.

20. The method of claim 19, wherein the dual percutaneous anchors are configured to osseointegrate over time with the recipient's skull after said attaching.

21. The method of claim 19, wherein the dual percutaneous anchors are fixed by one or more screws to the recipient's skull.

22. The method of claim 19, wherein the dual percutaneous anchors are attached to one or more plates fixed to the recipient's skull.

23. The method of claim 22, wherein said one or more plates are configured to osseointegrate with the recipient's skull over a period of time.

24. A bone conduction device for enhancing the hearing of a recipient, having dual percutaneous anchors, comprising:
means for forming a mechanical coupling between the bone conduction device and the recipient's skull via the dual percutaneous anchors;
means for receiving an electrical signal representative of an acoustic sound signal;
means for generating mechanical forces substantially parallel to a recipient's skull when the bone conduction device is attached thereto, wherein the mechanical forces are representative of the received electrical signal; and
means for delivering said mechanical forces to the recipient's skull via the formed coupling.

25. The device of claim 24, further comprising:
means for securing the dual percutaneous anchors within to the bone conduction device.

26. The device of claim 24, further comprising:
means for attaching the dual percutaneous anchors to the recipient's skull.

* * * * *